United States Patent [19]

Kawano

[11] Patent Number: 5,382,246
[45] Date of Patent: Jan. 17, 1995

[54] DISPOSABLE DIAPER

[75] Inventor: Masashi Kawano, Tokyo, Japan

[73] Assignee: Koyo Disposable Goods Company, Japan

[21] Appl. No.: 584,562

[22] Filed: Sep. 18, 1990

[51] Int. Cl.⁶ .................... A61F 13/15; A61F 13/20
[52] U.S. Cl. .................... 604/385.2; 604/358; 604/385.1
[58] Field of Search ............ 604/385.1, 385.2, 358, 604/380

[56] References Cited

U.S. PATENT DOCUMENTS

| 4,037,602 | 7/1977 | Hawthorne | 604/380 X |
| 4,166,464 | 9/1979 | Korpman | 604/385.1 X |
| 4,285,343 | 8/1981 | McNair | 604/387 |
| 4,326,528 | 4/1982 | Ryan et al. | 604/385.2 |
| 4,397,645 | 8/1983 | Buell | 604/385.2 |
| 4,573,991 | 3/1986 | Pieniak et al. | 604/385.2 |
| 4,589,876 | 5/1986 | Van Tilburg | 604/393 X |
| 4,657,539 | 4/1987 | Hasse | 604/385.2 |
| 4,687,477 | 8/1987 | Suzuki et al. | 604/385.2 |
| 4,687,478 | 8/1987 | Van Tilburg | 604/387 |
| 4,695,278 | 9/1987 | Lawson | 604/385.2 |
| 4,704,116 | 11/1987 | Enloe | 604/385.2 |
| 4,710,187 | 12/1987 | Boland et al. | 604/385.2 |
| 4,759,754 | 7/1988 | Korpman | 604/387 |
| 4,808,177 | 2/1989 | DesMarias et al. | 604/385.2 X |
| 4,822,435 | 4/1989 | Igaue et al. | 604/385.2 |
| 4,834,740 | 5/1989 | Suzuki et al. | 604/385.2 |
| 4,842,596 | 6/1989 | Kielpikowski | 604/385.2 |
| 4,900,317 | 2/1990 | Buell | 604/385.2 X |
| 4,911,701 | 3/1990 | Mavinkurve | 604/385.2 |
| 4,988,344 | 1/1991 | Reising et al. | 604/380 X |
| 5,188,626 | 2/1993 | Toyoda et al. | 604/358 X |

FOREIGN PATENT DOCUMENTS

| 4018097 | 8/1991 | Germany | 604/385.2 |
| 1164492 | 9/1969 | United Kingdom | 604/380 |
| 2212382 | 12/1988 | United Kingdom | 604/385.2 |

Primary Examiner—Randall L. Green
Assistant Examiner—Elizabeth M. Burke
Attorney, Agent, or Firm—Skjerven, Morrill, MacPherson, Franklin and Friel; Takahashi & Takahashi

[57] ABSTRACT

A disposable diaper, having a body covering a desired part of the human body, a central absorber provided at the center of the body, expandable portions provided to the opposite sides of the central absorber, and peripheral absorbers extending outside the expandable portions. The diaper has an improved fit and feel, and an improved closeness of boundary fit so as to better prevent urine leaks.

10 Claims, 6 Drawing Sheets

DISPOSABLE DIAPER

BACKGROUND OF THE INVENTION

The present invention relates to a disposable diaper.

A disposable diaper comprises a water-permeable surface sheet, a water-impermeable back sheet and an absorbent material sandwiched therebetween. The urine absorption capacity of the disposable diaper depends on the volume of the absorbent material.

The urine absorption force of a disposable diaper must be high at the pubic region. In order to secure the high urine absorption force at the pubic region, a pubic region fitting portion of a prior-art disposable diaper has been broad.

However, such a disposable diaper with the broad pubic-region-fitting portion entails a drawback in that it makes it difficult or impossible to achieve a closeness of fit in the pubic region, and promotes leakage therefrom. That is, the broad pubic-region-fitting portion of the diaper causes a pocket-shaped space thereby producing a gap between the wearer and the diaper and causing urine to leak laterally from the diaper.

In an attempt to solve this problem workers in the art have selected the width of an absorbent material of the pubic region fitting portion to be 150-200 mm to improve closeness of fit to the pubic region. Other workers have attempted to improve the urine diffusivity through the thickness of the absorbent material. Still other workers have devised a disposable diaper which had a double pubic layer in an attempt to reduce the lateral urine leak.

However, so far these changes have not sufficiently prevented urine from leaking laterally from the diaper. In particular, it has been difficult to prevent urine from leaking laterally from the pubic region fitting portion when the wearer is lying on his or her side.

SUMMARY OF THE INVENTION

A primary object of the present invention is to provide a disposable diaper which can control lateral urine leakage from the pubic region fitting portion of the diaper.

Another object of the present invention is to provide a disposable diaper superior in fit and closeness.

In order to achieve these objects, a disposable diaper of the present invention comprises: a body covering a desired part of the human body; a central absorber provided at the center of the body; expandable portions provided to the opposite sides of the central absorber; and peripheral absorbers extending outside the expandable portions. In accordance with the present invention, the peripheral absorbers of the disposable diaper increase the urine absorption capacity of the diaper and also absorb any urine leaking from the central absorber. Thus, the width of the central absorber fits the human body so that the diaper has an improved fit and closeness. Consequently, the present invention has an improved fit and urine absorption capability. In particular, lateral urine leakage when the wearer is lying on his or her side is reduced.

DESCRIPTION OF THE PREFERRED EMBODIMENTS

Figure 1:
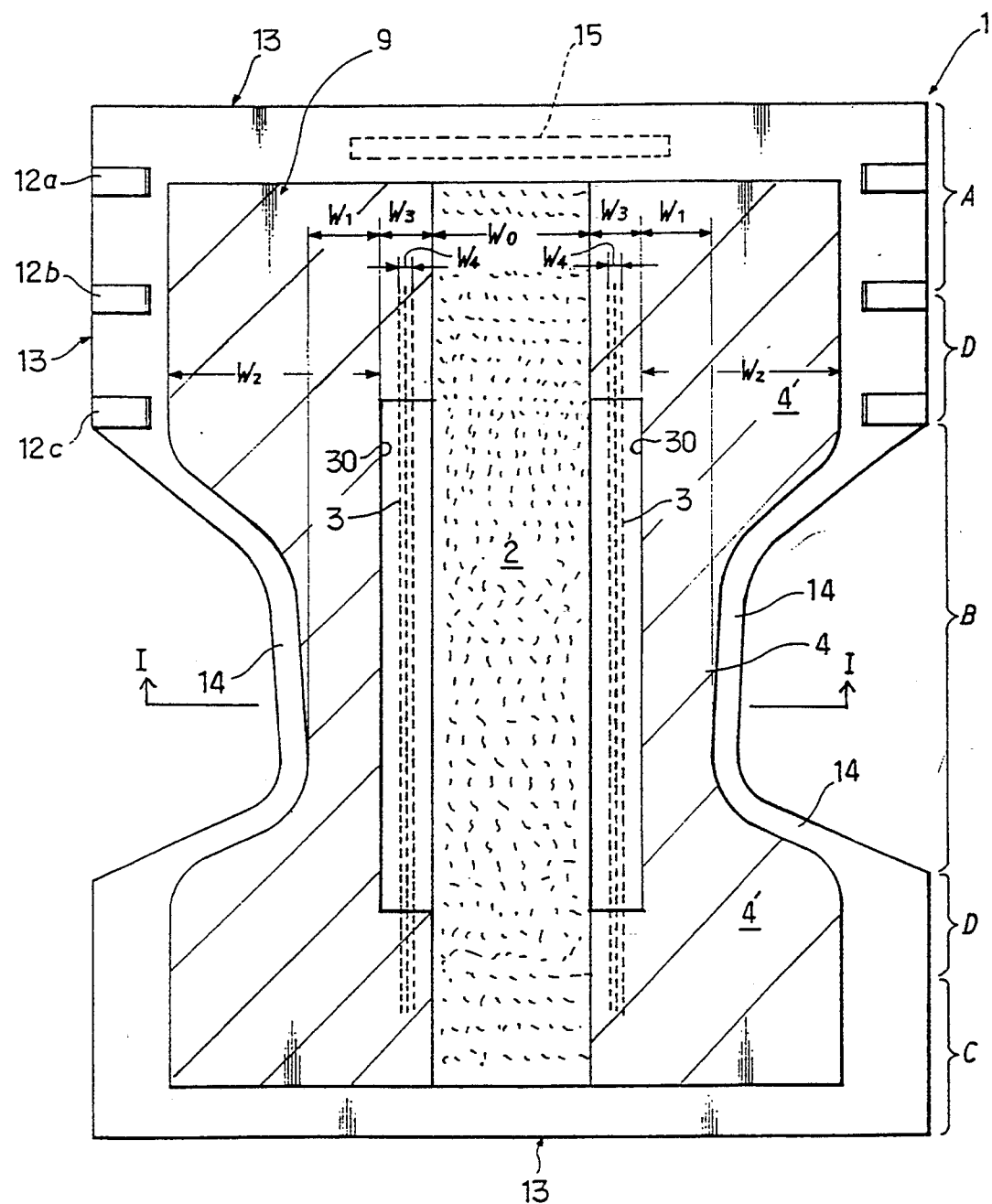
FIG. 1 is a plan view of a disposable diaper of a first embodiment of the present invention.
Figure 2:
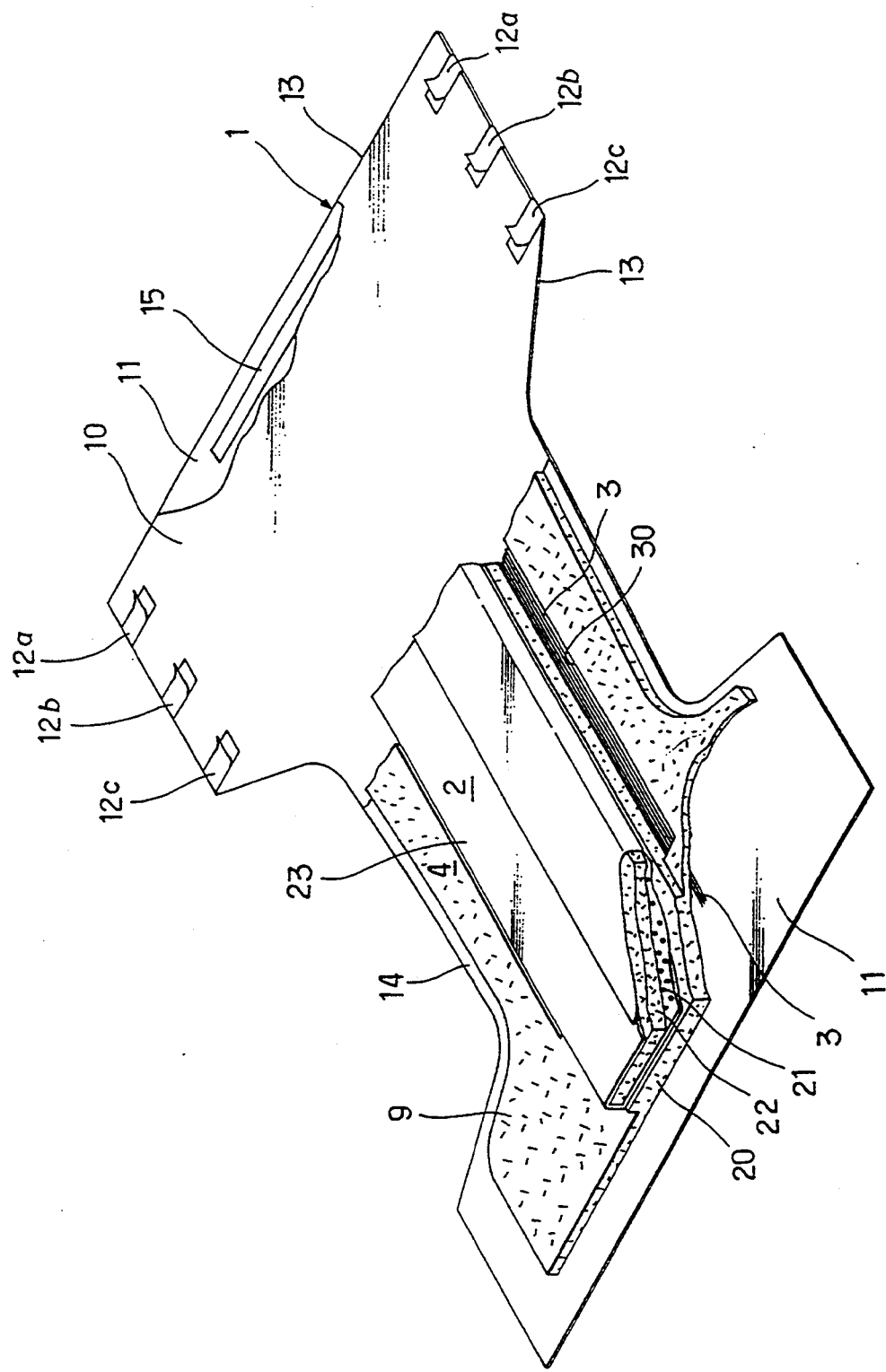
FIG. 2 is a perspective view of the disposable diaper of FIG. 1.
Figure 8:
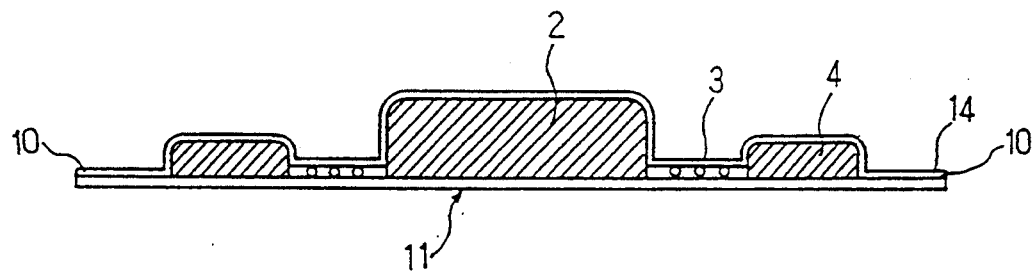
FIG. 8 is a section through the diaper taken along the line I—I in FIG. 1.

A first embodiment of the present invention will be described with reference to FIGS. 1-5 and 8. As shown in FIGS. 1, 2 and 8, the body 1 of a disposable diaper comprises a water-permeable surface sheet 10 made of nonwoven fabric and a water-impermeable back sheet 11 made of polyethylene film, the two sheets 10 and 11 together having a double-ply structure. The surface sheet 10 and back sheet 11 sandwich a central absorber 2, expandable strips 3 and peripheral absorbers 4 therebetween. Referring to FIG. 1 the body 1 comprises a rear portion A to be situated on the back of the hip, an intermediate portion B to be situated in fitting on the pubic region of the wearer and the front surfaces of the thighs, and a front portion C to be situated in fitting on the abdomen. In the first embodiment, the body 1 also comprises two extension portions D, one extending between the intermediate portion B and rear portion A and the other extending between the intermediate portion B and from portion C. A width of almost all of the intermediate portion B is less than those of the rear portion A, front portion C and extension portion (hereafter "extension") D.

The central absorber 2 is situated on the axis of the body 1 and extends the length of a layer 9 made of flake-shaped pulp. The width WO of the central absorber 2 must be selected to fit the size of the wearer and may be in the range 100-200 mm. In particular, that of the central absorber 2 of an adult disposable diaper is preferably selected 120-180 mm for best fit to the pubic region.

Each side of the central absorber 2 has an expandable strip 3 made of an elastic strand fastened to the back sheet 11 and extending along a portion of the length thereof. The expandable strips 3 fit the bases of the thighs to bring the central absorber 2 into close contact with the pubic region. The number of strands of the expandable strip 3 is preferably 1-5. The width W4 of the expandable strip 3 is preferably 5-10 mm. The expandable strip 3 is preferably spaced from the central absorber 2 and peripheral absorber 4 with clearances equalling the width W4 of the expandable strip 3 so as to allow adequate room for the expandable strip to operate. The width W3 of either slot 30 is preferably selected 15-30 mm in response to the width W4 of the expandable strip 3. The length of the expandable strip 3 in the full extending position must be 100 mm or more. In the first embodiment, the expandable strip 3 extends oppositely from the intermediate portion B (hereafter "intermediary") through the extension portions D to the rear portion A and front portion C.

Almost all of the peripheral absorber 4 is situated outside either expandable strip 3 relative to the position of the central absorber and is in close contact with the thigh when the diaper is worn. The peripheral absorber 4 extends axially into both the front portion C (hereafter "front") and rear portion A (hereafter "rear") to terminate in opposite expanded peripheral absorbers 4' provided in the front C and rear A, as shown by the hatched portion hatching of FIG. 1.

Figure 5:
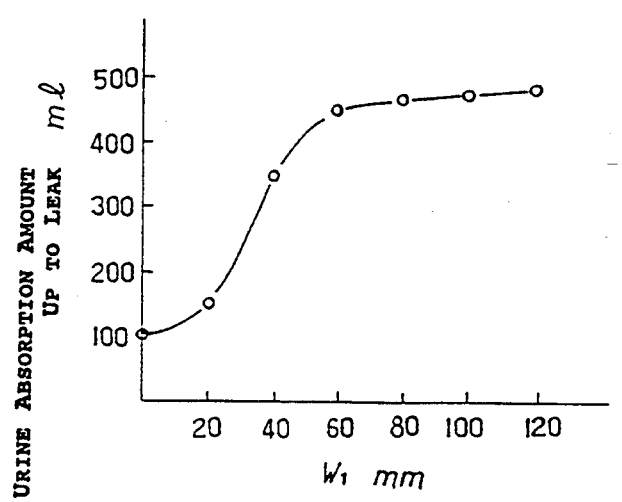
FIG. 5 is a graph of a relationship between the width and urine absorption capacity of a peripheral absorber.

The greater the minimum width W1 of the main body of the peripheral absorber 4, the higher the urine absorption capacity of the peripheral absorber 4. However, the increase in urine absorption capacity of the peripheral absorber 4 with 80 mm or more in width W1 is low as shown in the graph of FIG. 5. Thus, the width W1 is preferably 40–100 mm. As shown in FIG. 1, the width of the main body of the peripheral absorber 4 slightly increases towards the rear A and, in the first embodiment, at about a 4 degree angle. The value of the width W1 of the main body of the peripheral absorber 4 provides the width W1 of the narrowest portion of the peripheral absorber 4. The width W2 of the expanded peripheral absorber 4' provided in each extension D must be at least twice the width W1. The width W2 is preferably 80–200 mm. In the first embodiment, parts of the expanded peripheral absorber 4' provided at each extension D, rear A and front C have the width W2.

As shown in FIG. 2, the peripheral absorber 4 including the expanded peripheral absorbers 4' is made with a one-piece flake-shaped-pulp layer 9. The flake-shaped-pulp layer 9 comprises a thickened portion 20 providing an underlying layer of the central absorber 2. The central absorber 2 comprises this thickened portion 20, a superabsorbent polymer layer 21 laminated on the thickened portion 20, and an assembly of a flake-shaped-pulp layer 22 and a cover paper 23 packing the layer 22, the assembly being laminated on the superabsorbent polymer layer 21.

The flake-shaped-pulp layer 9 has two slots 30 therein so as not to impair the elasticity of the expandable strips 3. The slots 30 are in contact with and extend along the opposite sides of the central absorber 2 so that the length of each slot 30 essentially equals that of the intermediary B.

Figure 3:
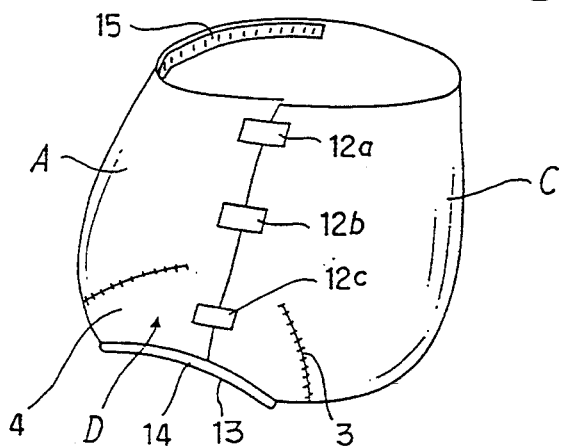
FIG. 3 is a perspective view of the diaper in fitting position.
Figure 4:
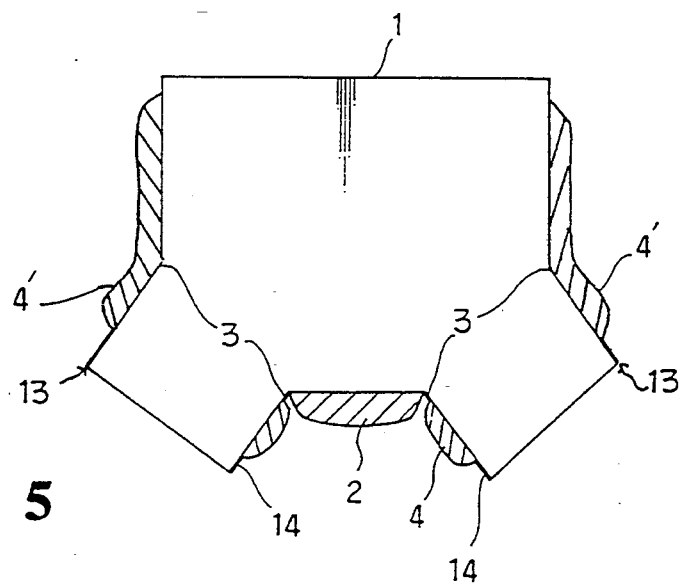
FIG. 4 is a longitudinal section through the diaper of FIG. 3.

As shown in FIGS. 2–4, the body 1 has a side flap 14 made with only parts of the surface sheet 10 and the back sheet 11 and surrounding the flake-shaped-pulp layer 9. The edges of the surface sheet 10 and back sheet 11 providing the edge of the side flap 14 are bonded to each other so as to provide a sealed edge 13. The sealed edge 13 prevent urine from leaking through a gap between the surface sheet 10 and back sheet 11.

Either side of the rear A of the body 1 has side tapes 12a and 12b and 12c fastening the rear A and front C when the disposable diaper is worn. Either side of the extension D adjoining the rear A has a side tape 12c fastening the extension D adjoining the rear A to the extension D adjoining the front C so as to bring the peripheral absorbers 4 into close contact with the thighs. The top edge of the rear A has a waist gather 15 attached thereto which is in close contact with the waist of the wearer so as to prevent urine from leaking from the back edge of the diaper when the wearer is lying on his or hear back.

FIGS. 3 and 4 illustrate the disposable diaper when in fitting position. As shown in FIG. 3, the side tapes 12a and 12b fasten the rear A and front C. The side tapes 12c fasten the extension D to the thighs. The side tapes 12c can easily adjust their fastenings so that the peripheral absorbers 4 are in close contact with the thighs. The expandable strips 3 tighten the bases of the thighs and the width WO of the central absorber 2 is large enough for a close fit to the human body. Thus, the disposable diaper has a good fit in close contact with the human body. The disposable diaper of the first embodiment has no gap between it and the human body unlike prior-art disposable diapers, such that no urine leaks laterally from the pubic-region of the diaper. In addition, the peripheral absorbers 4 are in close contact with the thighs so as to absorb urine which may leak from the expandable strips 3. That is, pressure from the body of the wearer may transfer some urine which has not been absorbed by the central absorber 2 to the rear A and front C, and the peripheral absorbers 4 with the expanded absorbers 4' securely absorbing the transferring urine. In addition, the body 1 has the sealed edge 13, so that the surface sheet 10 and back sheet 11 provide no gap therebetween to allow a urine leak.

Figure 6:
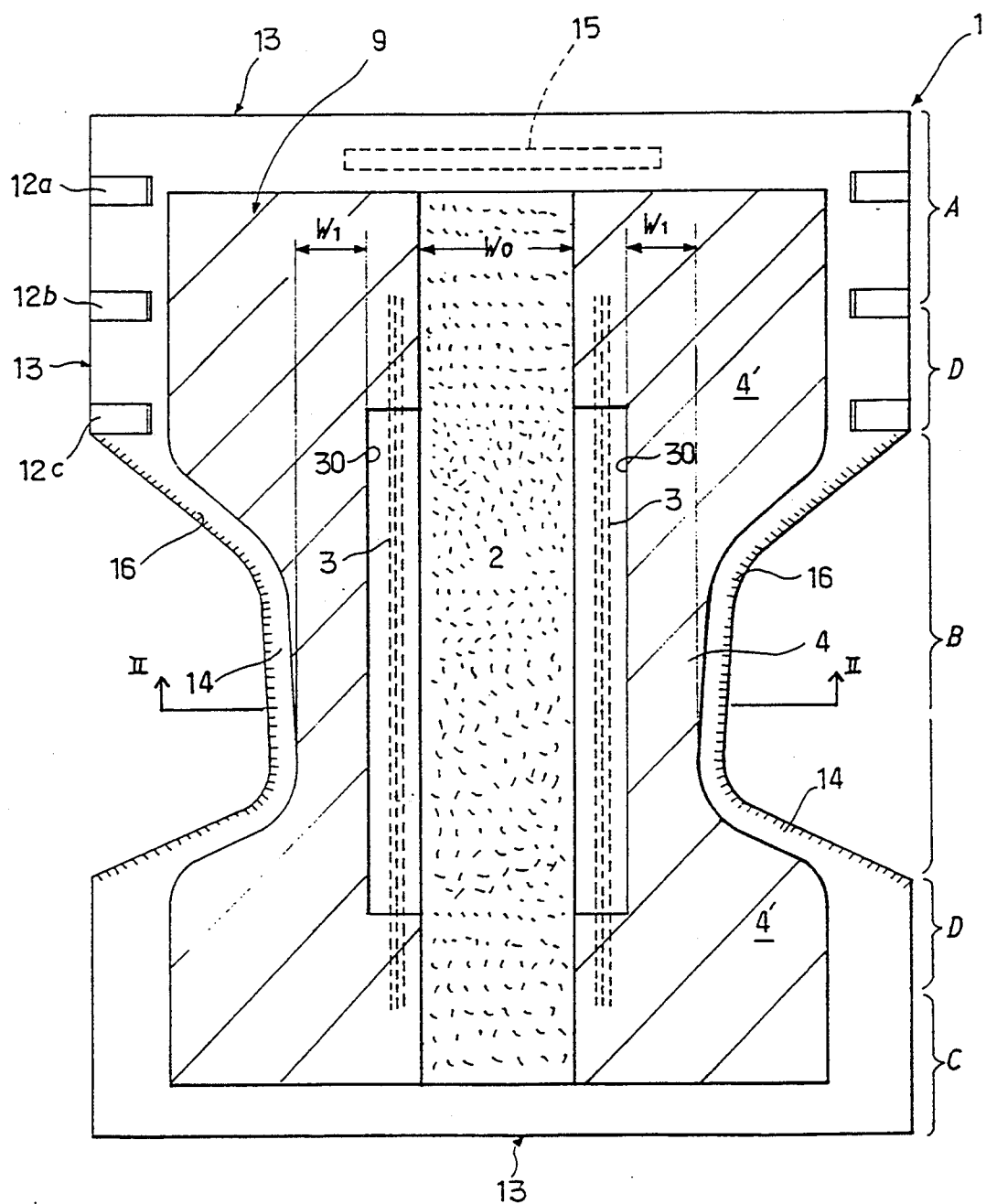
FIG. 6 is a plan view of a disposable diaper of a second embodiment of the present invention.
Figure 9:
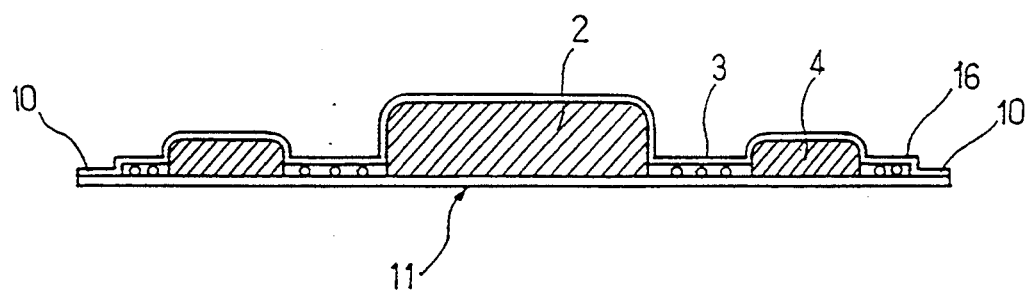
FIG. 9 is a section of the diaper taken along the line II—II in FIG. 6.

A disposable diaper of a second embodiment of the present invention is shown in FIGS. 6 and 9. The second embodiment comprises, in addition to the arrangement of the first embodiment, an intermediary B with side flaps 14 which thigh-fitting gathers 16 are attached. In the second embodiment, the expandable strips 3 tighten to the bases of the thighs, and the thigh-fitting gathers 16 tighten to the lower parts of the thighs adjoining the bases of the thighs so that the disposable diaper can provide an improved fit and have an improved urine leak prevention capability.

Figure 7:
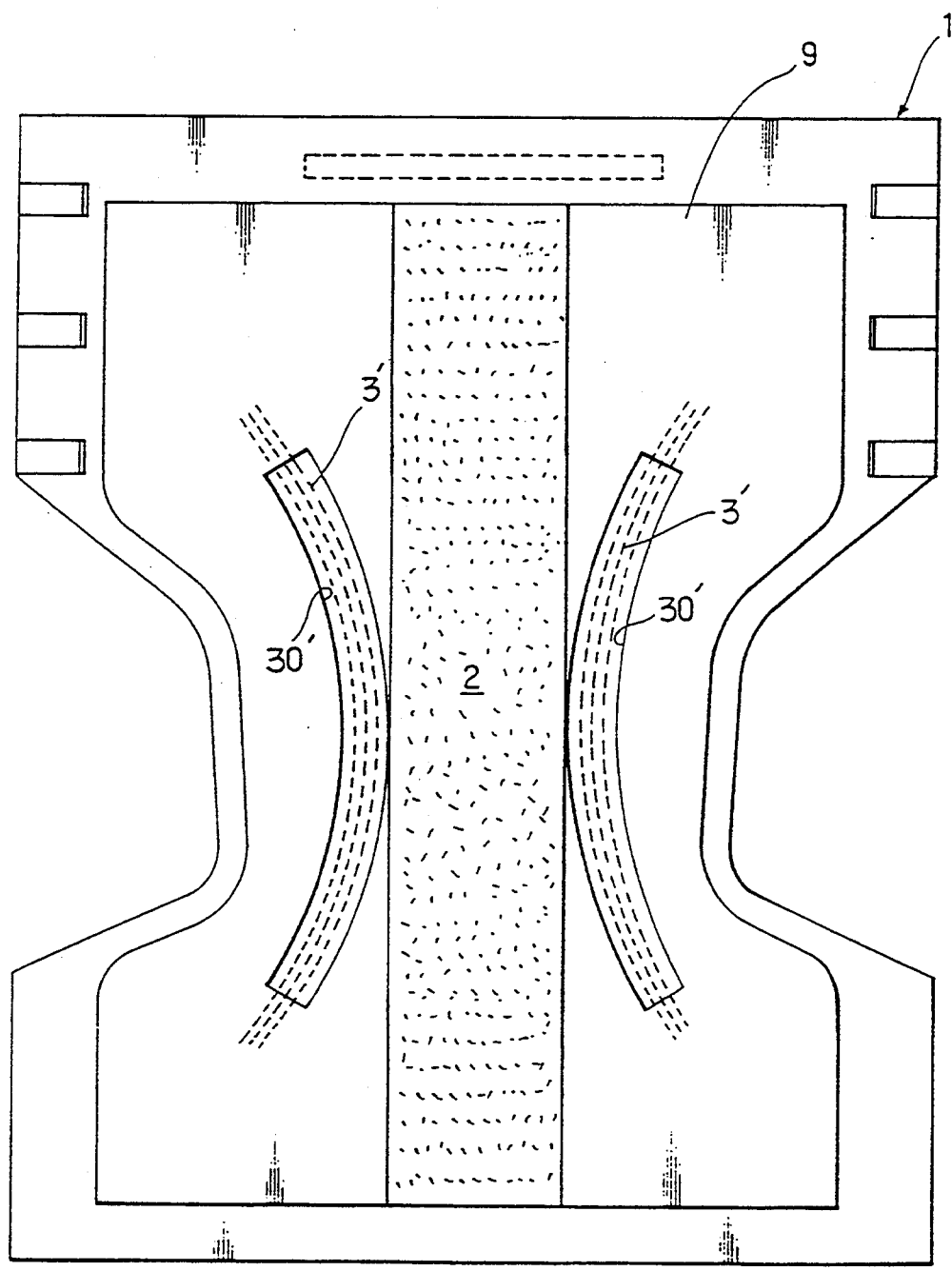
FIG. 7 is a plan view of a disposable diaper of a third embodiment of the present invention.

A disposable diaper of a third embodiment of the present invention is shown in FIG. 7. This embodiment comprises expandable strips 3' the distance between which increases at points farther from the center of the diaper so that the disposable diaper can fit better to the thighs. Correspondingly, the distance between the arc-shaped slots 30' correspondingly increases at points farther from the center of the diaper. The remaining structure of the third embodiment of FIG. 7 are the same as those of the first embodiment of FIG. 1, and, thus, almost all of the labels indicating remaining structures of the third embodiment are eliminated.

The above arrangements of the first to third embodiments are applicable to both infant and adult disposable diapers.

Test

Urine leaks in on-the-back position and on-the-side position of the wearer were measured with an life sized model of the human body connected to a urine speed controller, an artificial urine ejector and an electric moisture sensor connected to the upper surface of a leak detector plate. Artificial urine was ejected at a 15 ml/s flow rate. The test used disposable diapers of the first to third embodiments of FIGS. 1, 6 and 7 and prior-art disposable diapers. Table 1 shows the results of the test. As seen in Table 1, the disposable diapers of the present invention have absorption capacity which is essentially twice those of the prior-art disposable diapers so that urine leaks from the disposable diapers according to the teachings of the invention are reduced.

TABLE 1

|  | | FIG. 1 first embodiment Absorption amount ml | FIG. 7 second embodiment Absorption amount ml | FIG. 7 third embodiment Absorption amount ml | Prior Art Absorption amount ml |
|---|---|---|---|---|---|
| On-the-back lying position | 1 | 950 | 822 | 932 | 352 |
|  | 2 | 828 | 899 | 851 | 705 |
|  | 3 | 895 | 960 | 900 | 690 |
|  | 4 | 803 | 795 | 790 | 423 |
|  | 5 | 922 | 901 | 849 | 746 |
| On-the-side lying position | 1 | 430 | 410 | 503 | 146 |
|  | 2 | 410 | 433 | 420 | 204 |
|  | 3 | 425 | 409 | 498 | 200 |
|  | 4 | 413 | 395 | 430 | 128 |
|  | 5 | 400 | 401 | 415 | 235 |

What is claimed:

1. A disposable diaper comprising:
   a liquid impermeable outer sheet;
   a liquid permeable inner sheet attached to said outer sheet so as to form an enclosed space;
   a central absorber in said enclosed spaced;
   first and second elastic strips, said first elastic strip located between said central absorber and a first outer edge of said enclosed space, said second elastic strip located between said central absorber and a second outer edge of said enclosed space, said second outer edge being opposite said first outer edge; and
   first and second peripheral absorbers in said enclosed space, said first peripheral absorber located between said first elastic strip and said first outer edge of said enclosed space, said second peripheral absorber located between said second elastic strip and said second outer edge of said enclosed space, portions of said central absorber and first peripheral absorber defining a first space therebetween in which is disposed at least a portion of said first elastic strip, portions of said central absorber and second peripheral absorber defining a second space therebetween in which is disposed at least a portion of said second elastic strip.

2. A disposable diaper as recited in claim 1, wherein said central and peripheral absorbers are made of a thickened layer of absorbent material and each of said elastic strips includes a plurality of elastic strands fastened to said liquid impermeable outer sheet.

3. A disposable diaper as recited in claim 2, wherein said central and peripheral absorbers are made of one layer of absorbent material, and wherein said layer of absorbent material defines said first and second spaces at opposite sides of said central absorber.

4. A disposable diaper as recited in claim 1, wherein said central and peripheral absorbers are made of one layer of absorbent material, and wherein said layer of absorbent material defines said first and second spaces at opposite sides of said central absorber.

5. A disposable diaper as recited in claim 1, wherein the distance between the first and second elastic strips is at a minimum between a center portion of the first elastic strip and a center portion of the second elastic strip, and increases in both directions from the center portions, along the first and second elastic strips.

6. A disposable diaper as recited in claim 1, further comprising third and fourth elastic strips, said third elastic strip located between said first peripheral absorber and said first outer edge, said fourth elastic strip located between said second peripheral absorber and said second outer strip.

7. A disposable diaper to be worn by a wearer, said diaper comprising:
   first absorbent means having first and second edges for providing a primary absorbent body for absorption of waste material;
   first and second elastic sealing means coupled to said first absorbent means for stretching to precisely fit legs of the wearer at a groin area of the wearer so as to form at least a partially sealed area in which said first absorbent means resides, said at least partially sealed area including the groin area of the wearer of said diaper;
   secondary absorbent means for providing backup absorbent capacity for any waste material which escapes past said first and second elastic sealing means, said secondary absorbent means having a first portion adjacent to said first elastic sealing means and a second portion adjacent to said second elastic sealing means;
   at least a portion of said first elastic sealing means being positioned between said first absorbent means and said first portion of said secondary absorbent means, at least a portion of said second elastic sealing means being positioned between said first absorbent means and said second portion of said secondary absorbent means.

8. A disposable diaper as in claim 7 wherein said first portion of said secondary absorbent means is configured to contact an entire circumference of a first leg of the wearer, and said second portion of said secondary absorbent means is configured to contact an entire circumference of a second leg of the wearer.

9. A disposable diaper as in claim 7 wherein said first and second elastic sealing means are arcuate in shape.

10. A disposable diaper as in claim 7 further comprising third and fourth elastic sealing means for forming an outer seal around at least part of a circumference of the legs of the wearer, said third elastic sealing means located between said first portion of said secondary absorbent means and an edge of said diaper, said fourth elastic sealing means located between said second portion of said secondary absorbent means and an opposite edge of said diaper.

* * * * *